(12) United States Patent
Sun et al.

(10) Patent No.: US 8,598,401 B2
(45) Date of Patent: Dec. 3, 2013

(54) METHOD FOR ENHANCING THE PERFORMANCE OF A CATALYZED REACTION

(75) Inventors: Bing Sun, South Barrington, IL (US); Joseph Edward Zimmermann, Arlington Heights, IL (US); Michael Vetter, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 563 days.

(21) Appl. No.: 12/827,200

(22) Filed: Jun. 30, 2010

(65) Prior Publication Data

US 2012/0004488 A1 Jan. 5, 2012

(51) Int. Cl.
*C07C 5/333* (2006.01)

(52) U.S. Cl.
USPC ........... 585/659; 585/501; 585/654; 585/658; 585/910

(58) Field of Classification Search
USPC .......................... 585/501, 658, 659, 654, 910
See application file for complete search history.

(56) References Cited

U.S. PATENT DOCUMENTS

| | | | | |
|---|---|---|---|---|
| 2,440,525 | A | * | 4/1948 | Roetheli ................ 585/628 |
| 2,820,072 | A | * | 1/1958 | Wood et al. ............ 585/313 |
| 2,982,798 | A | * | 5/1961 | Hachmuth et al. ..... 585/628 |
| 3,288,878 | A | * | 11/1966 | Hachmuth ............. 585/659 |
| 3,978,150 | A | * | 8/1976 | McWilliams, Jr. ..... 585/659 |
| 4,341,911 | A | | 7/1982 | Vora |
| 4,376,225 | A | | 3/1983 | Vora |
| 4,523,045 | A | | 6/1985 | Vora |
| 4,615,792 | A | | 10/1986 | Greenwood |
| 5,130,106 | A | * | 7/1992 | Koves et al. ............ 422/216 |
| 5,254,788 | A | | 10/1993 | Gartside et al. |
| 5,491,274 | A | | 2/1996 | Minkkinen et al. |
| 6,432,369 | B1 | | 8/2002 | Mulvaney, III et al. |
| 6,472,577 | B1 | * | 10/2002 | Zimmermann et al. ... 585/441 |
| 6,602,483 | B2 | | 8/2003 | Heyse et al. |
| 7,091,392 | B2 | | 8/2006 | Abdulwahed et al. |
| 2009/0264692 | A1 | | 10/2009 | Welch et al. |

OTHER PUBLICATIONS

Annaland, "A novel reverse flow reactor coupling endothermic and exothermic reactions: An experimental study", Chemical Engineering Science, vol. 57, pp. 4967-4985, 2002.

Sanfilippo, et al., "Dehydrogenation of paraffins: synergies between catalyst design and reactor engineering", Catalysis Today, vol. 111, pp. 133-139, 2006.

Robertson, et al., "One Multivariable Controller Increased Capacity of an Oleflex(TM)/MTBE Complex", NPRA 1996 Annual Meeting (San Antonio Mar. 17-19, 1996) Paper (ISSN 0470-200X) Am-96-42, National Petroleum Refiners Association, pp. 1-18.

Bhasin, et al., "Dehydrogenation and oxydehydrogenation of paraffins to olefins", Applied Catalysis A: General, vol. 221, pp. 397-419, 2001.

Kotelnikov, et al., "Application of FBD processes for C3-C4 olefins production from light paraffins", Studies in Surface Science and Catalysis, vol. 147, pp. 67-72, 2004.

* cited by examiner

*Primary Examiner* — In Suk Bullock
*Assistant Examiner* — Bradley Etherton
(74) *Attorney, Agent, or Firm* — Arthur E Gooding

(57) ABSTRACT

A method for improving performance of a catalyzed reaction carried out in a moving bed system having a reaction zone. A process stream is introduced into the reaction zone at a temperature, and the temperature of the catalyst introduced to the reaction zone is different from the process stream introduction temperature to increase conversion.

10 Claims, No Drawings

METHOD FOR ENHANCING THE PERFORMANCE OF A CATALYZED REACTION

FIELD

The invention relates generally to a method for enhancing the performance of a catalyzed reaction system. More particularly, the invention relates to a method for enhancing system performance of a catalyzed reaction system by controlling the temperature of the catalyst.

DESCRIPTION OF RELATED ART

In many industries, like the petrochemical and chemical industries for instance, processes employ reactors in which chemical reactions are carried out in the components of one or more reaction fluids in contact with a catalyst under given temperature and pressure conditions. Most of these reactions are either exothermic or endothermic and therefore generate or absorb heat to various extents. The heating or chilling effects associated with exothermic or endothermic reactions can positively or negatively affect the operation of the reaction zone. The negative effects can include, but are not limited to, poor product production, deactivation of the catalyst, production of unwanted by-products, and, in extreme cases, damage to the reaction vessel and associated piping. More typically, the undesired effects associated with temperature changes will reduce the selectivity or yield of products from the reaction zone.

Often, catalytic reactors used in the petrochemical and chemical industries are tubular arrangements that have fixed or moving catalyst beds. Such reactors may be radial flow reactors, in which the reaction fluids flow radially through an annulus containing the catalyst. The geometry of tubular reactors poses layout constraints that require large reactors or limit throughput.

One solution to the problem has been the indirect heating of reactants, catalysts, or both, within a reaction zone with a heating or cooling medium. Increasing the temperature of the reactants by heating the reactants before the reaction zone often leads to degradation of the feedstock, such as, for example, by thermal cracking or polymerization. Such degradation also often leads to equipment fouling and malfunctions. Another solution is to introduce, as part of the process stream, a relatively significant quantity of material to act as a heat carrier. However, this approach requires larger product recovery section and energy use to heat and move the heat carrier through the system, and may entail other equipment changes.

One method for indirect heat exchange employs thin plates to define alternate channels that retain catalyst and reactants in one set of channels and a heat transfer fluid in alternate channels for indirectly heating or cooling the reactants and catalysts. Heat exchange plates in these indirect heat exchange reactors can be flat or curved and may have surface variations such as corrugations to increase heat transfer between the heat transfer fluids and the reactants and catalysts.

Most catalysts for the reaction of hydrocarbons are susceptible to deactivation over time. Deactivation may occur because of an accumulation of deposits that cause deactivation by blocking active pore sites or catalytic sites on the catalyst surface. Coke is an example of one such deposit. Also, if the catalyst contains compounds that can exist in oxidized or reduced state, typically one of these states is more active and selective to the preferred reaction product. Thus, when catalyst is deactivated, reconditioning or regenerating the catalyst to restore the activity of the catalyst is required. For example, coke normally is removed from the catalyst by contact of the coke-containing catalyst at high temperature with an oxygen-containing gas to combust or remove the coke in a regeneration process. Catalysts also can be reduced or oxidized, as required, in processes known to the skilled practitioner. The regeneration process can be carried out in situ or the catalyst may be removed from a zone in which the hydrocarbon conversion takes place and transported to a separate regeneration zone for coke removal.

Reaction zones containing a moving bed of catalyst, and arrangements for continuously or semi-continuously moving catalyst particles from one reaction zone to another or from a reaction zone to a regeneration zone and then back to a same or different reaction zone, are well known. In such systems, catalyst often is transferred out of the reaction zone under gravity flow by removing catalyst from the bottom of the reaction zone. Similarly, catalyst is transferred into the reaction zone by adding catalyst to the top of the zone.

SUMMARY OF THE INVENTION

Aspects of this invention relate to a method for enhancing the performance of a catalyzed reaction system. In particular, the invention relates to a method for indirectly controlling the temperature of catalyst in a reactor. More particularly, the invention relates to a method for indirectly heating catalyst to enhance system performance.

DETAILED DESCRIPTION

The invention relates to a method for enhancing the performance of a catalyzed reaction system by controlling the temperature of catalyst in a reactor. More particularly, the invention relates to a method for indirectly heating catalyst to enhance system performance. The invention thus relates to a number of catalyzed reaction systems.

Catalyzed reactions often are exothermic or endothermic reactions, but an essentially constant temperature often is desired to obtain maximum conversion. In other catalyzed reactions, it may be preferred to maintain a selected temperature profile as the reaction progresses.

Catalyzed reactions may be carried out in a single reaction zone or plural reaction zones in series. Plural reactors in series often are used to enable temperature adjustment of reactants or catalyst between zones. Plural zones may be in a single subdivided reactor vessel, or may be in separate vessels.

Catalyzed reactions are carried out in the presence of a wide variety of catalysts. Typically, catalysts used in the petrochemical and chemical industries are solid. Although liquids and gases can serve as catalyst, solids typically are used.

Catalyzed reactions may be carried out in a reactor having a fixed bed of catalyst, or the catalyst may be moving within the reactor. Catalyst in a moving bed can be fluidized, or can flow downward by gravity.

Many catalyzed reactions require periodic catalyst regeneration to remove contaminants or deposits, to restore the active state of a catalyst component, or both. The regeneration process can be carried out in situ, typically in a fixed bed system. Typically, in a moving catalyst system, the catalyst may be removed from the zone and regenerated in another zone.

Arrangements for continuously or semi-continuously (intermittently) removing catalyst particles from a bed in a reaction zone for transfer to another reaction zone, or for regenerating in a regeneration zone and then returning the catalyst to the same or a different reaction zone, are well known. In such reactors, catalyst often is transferred out of the reactor under gravity flow by removing catalyst from the bottom of the reaction zone and is transferred into the reactor by adding catalyst to the top. Catalyst also may be moved either parallel with or counter-current to reactant flow. Catalyst may be moved from reactor to reactor in a multiple-reactor system, or may be moved to a regeneration zone between reactors. Catalyst is introduced to a reaction zone at a temperature lower than or close to the temperature at which the process stream is introduced.

Embodiments of the invention relate to a method for enhancing the performance of a catalyzed reaction system by controlling the temperature of catalyst in a reactor. The invention therefore relates to systems in which an exothermic or endothermic reaction having any selected desired temperature profile is catalyzed by solids in a moving bed reaction zone or zones in series in which the catalyst is continuously or intermittently removed from a reaction zone and returned to the same or to another reaction zone, or is removed to a regeneration zone and then back to a reaction zone. In particular, embodiments of the invention are directed to systems in which reactant fluids flow radially through an annular bed of catalyst that is moving downwardly through the annulus. The reactant fluids, often called the process stream, includes fresh and recycled components.

For convenience, embodiments of the invention will be described with particularity with regard to an endothermic reaction, such as dehydrogenation of a paraffin, in a system having a plurality of reaction zones in series with a regeneration zone and in which embodiments of the invention are used to increase reaction zone and catalyst temperature to ameliorate the effect of the endothermic nature of the reaction on system performance, particularly on activity and selectivity. Paraffins having two or more carbon atoms, and more typically between 2 and about 8 carbon atoms, are catalytically dehydrogenated.

Often in such systems, the endothermic nature of the dehydrogenation reaction causes temperature gradients that introduce stress sufficient to damage the reactor vessel. In particular, reactor vessel internal features, such as the annular screen that retains catalyst, may be damaged by large temperature gradients in the system.

In embodiments of the invention, the regeneration zone has both a coke-removal zone and a reduction zone. Coke is removed from the catalyst, typically by oxidation or burning. However, the coke removal step typically also oxidizes the catalyzing metals on the catalyst. Thus, these catalyzing metals are reduced, or converted from an oxidized state to a reduced (base metal) state, in a reduction zone. The reduction zone thus is after the coke-burning zone, as the catalyzing metals likely will be oxidized in the coke burn, and hydrogenation will be necessary to restore the more active reduced metal state. Such reduction conveniently is done with hydrogen often obtained from the reaction zone effluent and typically purified to effectively reduce the catalyzing metal without depositing coke.

Details of embodiments of the invention will be described as they relate to a system in which catalyst is moved through plural reaction zones, to a regeneration zone, and then back to the first reaction zone. Thus, in embodiments of the invention, catalyst is moved from a regeneration zone to a first reaction zone, then to the second and third reaction zones in series, after which it is returned to the regeneration zone. Catalyst is removed from the bottom of the zone and transported to the top of the next zone. Catalyst introduced at the top of each reaction zone has higher activity than catalyst removed from the bottom of that zone. Catalyst removed for regeneration has higher activity than catalyst introduced at the top of that zone.

Each of the zones has an enclosed volume, often called a surge volume or a surge pot, at the top of the zone. In the first reactor, this volume serves as a reduction zone. For the other reactors, this volume contains catalyst but is not in a reaction zone. This volume serves to accommodate uneven catalyst flow by receiving catalyst and reserving some catalyst immediately at the point catalyst is introduced to the annulus. In this way, catalyst always is available for introduction to the annulus in the zone, yet the volume can accommodate a temporary flow of catalyst greater than that introduced to the annulus. Each zone also has a mechanism at the bottom to ensure that catalyst is properly supported in the annulus while metering flow out of the reactor at the appropriate rate. These and other designs are known to the skilled practitioner.

Embodiments of the invention relate to dehydrogenation of paraffin, which is an endothermic reaction that is controlled by equilibrium. Equilibrium conversion is limited by thermodynamics and increases with temperature. To achieve reasonable economic conversion, temperatures exceeding 550° C. typically are required, with even higher temperatures required for lighter paraffins.

The principal reactions in the dehydrogenation of propane or butane include catalytic and thermal dehydrogenation to form hydrogen and propylene, also commonly called propene, or butylenes, typically called butenes; thermal cracking, to form ethene and methane, and thermal degradation to form butyne, ethene, and hydrogen. As described herein, the thermal processes are not selective to propylene or to butylenes, and thus should be avoided.

As can be seen, high propane temperature away from catalyst increases undesirable side reactions. For example, reactant flow temperature is maintained below about 660° C., typically between about 600° C. and about 660° C., and more typically between about 620° C. and about 650° C. Above about 660° C., thermal cracking and degradation become sufficient to adversely impact the economics of the process. Below about 600° C., the reaction is slow and becomes commercially uneconomic. The skilled practitioner recognizes that the temperature at which thermal cracking becomes significant depends upon the paraffin. With the guidance provided herein, the skilled practitioner will be able to identify an appropriate operating temperature.

The skilled practitioner recognizes that both catalyst and process streams are re-heated between reaction zones. Similar heaters can be used for each of the feed heating and process stream re-heating steps. Indirect heating by heat exchange with other materials that are to be cooled also commonly is used. However, the thermal energy that can be introduced with each such feed and reactant heating step is limited to the energy available at a temperature less than the temperature at which thermal cracking becomes unacceptable, which is about 660° C. for propane.

The effluent from the last reaction zone comprises propylene or butylene, other hydrocarbons, and hydrogen. The effluent is separated into streams in accordance with the objectives of the operator, but typically includes a stream comprising unreacted feed (propane or butane) and a hydrogen stream. Unreacted propane or butane and other materials can be recycled, typically through the feed heater, and introduced to the first reaction zone. Hydrogen often is separately recovered and may be purified in known processes. Conveniently, the hydrogen stream is used, typically after purification, in the reduction zone to convert catalysis metals from the essentially inactive oxidized state to the active reduced state.

Catalyst from the bottom of the last reaction zone is regenerated, first by removal of coke, then by reduction with hydrogen. The hydrogen typically is heated to approximately 550° C. in the reduction zone, the temperature required to reduce the catalyst. Then, the hydrogen typically is heated close to the temperature at which the feed is to be introduced and used to re-heat the catalyst between reaction zones to avoid a changing thermal gradient that could cause mechanical damage on the screens in the reaction zone. The ratio of hydrogen flow to the hydrocarbon flow in the reactant stream typically is between about 0.3 and about 0.8, more typically between about 0.4 and about 0.75, and most typically between about 0.5 and 0.7. A hydrogen/hydrocarbon ratio of about 0.6 is very typical.

Other common operating conditions include the liquid hourly space velocity, or LHSV. For the catalyzed dehydrogenation of propane, the LHSV typically is between about 2 and about 4 $hr^{-1}$, and typically is 3 $hr^{-1}$. The skilled practitioner recognizes that various dehydrogenation catalysts are known. Typically, dehydrogenation catalyst contains platinum and perhaps other metals. Platinum and other metals require reduction after coke-burning in the regeneration zone.

The inventors have discovered that it is possible to enhance the performance of this catalyzed reaction system by increasing the temperature of the catalyst introduced to the top of each reaction zone. In this way, the quantity of thermal energy introduced into the reactor is increased without increasing the process flow temperatures, i.e., the temperatures to which the feed and the reactant flow between reaction zones are heated. Embodiments of the invention thus dissociate conversion from process flow temperature. Embodiments of the invention increase highly selective catalytic dehydrogenation without increasing thermal cracking and degradation. Embodiments of the invention thus are directed to an indirect way of providing thermal energy to the reaction system, i.e., a way that does not require additional heating of the reactant stream.

In accordance with embodiments of the invention, the hydrogen stream used to reduce the catalyst in the reduction zone and to re-heat the catalyst between reaction zones is heated to a temperature that can be higher than the temperature at which the process stream is introduced to the zone. Thus, system performance is enhanced by controlling the temperature of the catalyst, thus using the catalyst to introduce additional thermal energy into the reaction zoned to increase highly selective catalytic dehydrogenation. In embodiments of the invention, this improvement is obtained without heating the reaction streams, i.e., the feed and the reactant flowing between reaction zones, to a temperature at which thermal cracking becomes significant. In particular, because the hydrogen stream is essentially pure hydrogen, essentially devoid of any hydrocarbons, the temperature of the hydrogen, and thus of the catalyst, can be raised without degrading the catalyst or fouling equipment.

Embodiments of the invention require essentially no mechanical modification of the reaction apparatus, such as the reactor vessels, surge pots, piping, and the like. Thus, embodiments of the invention can be used in any system in which catalyst is reheated in a surge pot or similar feature. The only change is that additional energy must be transferred in the hydrogen heaters.

Embodiments of the invention are directed to a method of controlling the temperature of the hydrogen heating the catalyst, and thus of the catalyst itself, to a temperature up to about 670° C. Often, the temperature of the hydrogen is raised to a temperature about 10° C. greater than the process stream temperature. Typically, the temperature of the hydrogen heating the catalyst is raised to a temperature about 5° C. greater than the process stream temperature, and more typically the temperature of the hydrogen heating the catalyst is raised to a temperature about 3° C. greater than the process stream temperature. Very typically, a temperature of up to about 2° C. higher than the process stream temperature is used. In embodiments of the invention, the temperature of the catalyst, or the differences between the temperature of the catalyst and the process stream temperature for each of a series of reaction zones, need not be the same for each reduction zone and surge pot volume.

In accordance with embodiments of the invention, performance enhancements can be recognized or realized in a plurality of ways. For example, heating the catalyst to temperatures in excess of the process stream temperature will increase activity and selectivity, and so will provide increased product yield, decreased products of undesirable degradation or cracking, decreased fresh feed cost, and other indicia of performance that reduce cost. Also, the risk of reactor vessel damage caused by thermal stress is reduced.

With a typical LHSV and hydrogen/hydrocarbon ratio at a process stream temperature between about 600° C. and about 660° C., a 2° C. increase in the catalyst temperature in each reaction zone increases propane yield by about 0.5 percent over a system operating at increased process flow temperature sufficient to obtain the same propylene yield, because embodiments of the invention increase catalytic dehydrogenation without increasing thermal cracking and degradation.

Embodiments of the invention are easily carried out in most catalytic dehydrogenation reaction systems using moving bed reactors because the only equipment-based requirement to use embodiments of the invention is to ensure that the heaters can heat the hydrogen to the higher temperature before it enters the volume (reduction zone or surge pot) on top of the reaction zones.

In accordance with embodiments of the invention, performance enhancement can be recognized or realized in a plurality of ways. For example, heating the catalyst to a temperature above the temperature of the process stream will increase conversion, and so will provide increased product yield, decreased products of undesirable degradation or cracking, decrease fresh feed cost, and other performance indicia. Also, the risk of reactor damage caused by changing thermal stress is reduced.

EXAMPLE 1

Propane is dehydrogenated in the presence of platinum-containing catalyst. Four reaction zones in series and in separate vessels, with process stream reheaters between reaction zones, are used in series with a regeneration zone. The regeneration zone has a coke-burning portion and a catalyst reduction portion, in which the catalyst is reduced with essentially pure hydrogen.

Propane is introduced as part of the process stream at a LHSV of 3 $hr^{-1}$ at a temperature between 627° C. and 649° C. A hydrogen/hydrocarbon ratio of 0.6 is used, with the hydrogen, and therefore the catalyst introduced to each reaction zone, at the same temperature as the process stream temperature. The process is lined-out and reactor effluent composition is analyzed.

When the hydrogen temperature is raised to 2° C. higher than the temperature at which the process stream is introduced to that reaction zone, both propane conversion and propylene selectivity increase, with an overall propylene yield increase of about 0.5 percent. Thus, the enhanced system performance is realized in this operation in the form of less thermal cracking and degradation, as is indicated by the increase in propylene selectivity.

This example should be considered illustrative of embodiments of the invention, and should not be used to limit the invention in any way.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims. For example, embodiments of the invention can be directed to exothermic reactions, in which case catalyst is returned to the inventor cooler than typical return temperature. Also, embodiments of the invention include dehydrogenation of other paraffins, such as butane, pentane, and hexane.

The invention claimed is:

1. A method for improving performance of a catalyzed reaction carried out in a moving bed system in a reactor vessel comprising a reaction zone into which a process stream is introduced at a temperature, said method comprising controlling the temperature of the catalyst introduced to the reaction zone to a temperature different from the process stream introduction temperature to increase conversion, wherein the catalyst is controlled by heating the catalyst for an endothermic reaction, or cooling the catalyst for an exothermic reaction, in a surge pot or a reduction zone disposed within the reactor vessel and positioned above the catalyst bed, and wherein the bed system comprises more than one reaction zone in series and the catalyst is heated or cooled in the surge pot above the bed to a temperature up to about 10° C. different from the process stream introduction temperature for each reaction zone, and the differences between the temperature of the catalyst and the process stream introduction temperatures are not the same for all reaction zones.

2. The method of claim 1, wherein the catalyzed reaction is dehydrogenation of an alkane.

3. The method of claim 2, wherein the catalyzed reaction is dehydrogenation of propane or butane.

4. The method of claim 3, wherein the catalyst temperature is up to 670° C.

5. The method of claim 3, wherein the catalyst temperature is up to 10° C. higher than the process stream introduction temperature.

6. The method of claim 1 wherein the catalyzed reaction is exothermic.

7. A method for improving performance of a catalyzed endothermic reaction carried out in a moving bed system in a reactor vessel comprising a reaction zone into which a process stream is introduced at a temperature, said method comprising heating the temperature of the catalyst introduced to the reaction zone to a temperature above the process stream introduction temperature, wherein the catalyst is heated in a surge pot or a reduction zone disposed within the reactor vessel and positioned above the catalyst bed, wherein the bed system comprises more than one reaction zone in series and the catalyst is heated in the surge pot above the bed to a temperature up to about 10° C. greater than the process stream introduction temperature for each reaction zone, and the differences between the temperature of the catalyst and the process stream introduction temperatures are not the same for all reaction zones.

8. The method of claim 7, wherein the catalyzed reaction is dehydrogenation of an alkane.

9. The method of claim 8, wherein the catalyzed reaction is dehydrogenation of propane or butane.

10. The method of claim 7, wherein the catalyst temperature is up to 670° C.

* * * * *